(12) United States Patent
Li et al.

(10) Patent No.: US 12,145,979 B2
(45) Date of Patent: Nov. 19, 2024

(54) COMBINATION OF PVY MONOCLONAL ANTIBODIES CAPABLE OF RECOGNIZING DIFFERENT ANTIGENIC DETERMINANTS, AND USE THEREOF

(71) Applicant: Shandong Agricultural University, Tai'an (CN)

(72) Inventors: Xiangdong Li, Tai'an (CN); Zhiyong Yan, Tai'an (CN); Cuiling Zhao, Tai'an (CN); Qing Zhu, Tai'an (CN); Xiuqi Mu, Tai'an (CN); Yanping Tian, Tai'an (CN); Chao Geng, Tai'an (CN)

(73) Assignee: SHANDONG AGRICULTURAL UNIVERSITY, Tai'an (CN)

( * ) Notice: Subject to any disclaimer, the term of this patent is extended or adjusted under 35 U.S.C. 154(b) by 0 days.

(21) Appl. No.: 18/384,035

(22) Filed: Oct. 26, 2023

(65) Prior Publication Data
US 2024/0239872 A1  Jul. 18, 2024

(30) Foreign Application Priority Data

Jan. 17, 2023 (CN) .......................... 202310062606.7

(51) Int. Cl.
*C07K 16/10* (2006.01)
*G01N 33/569* (2006.01)

(52) U.S. Cl.
CPC ....... *C07K 16/10* (2013.01); *G01N 33/56983* (2013.01); *C07K 2317/565* (2013.01)

(58) Field of Classification Search
CPC .......................... C07K 16/10; G01N 33/56983
See application file for complete search history.

(56) References Cited

FOREIGN PATENT DOCUMENTS

| CN | 108136015 | 6/2018 |
|---|---|---|
| CN | 112552396 | 3/2021 |
| KR | 10-1960968 | 3/2019 |
| WO | 2022-150740 | 7/2022 |

OTHER PUBLICATIONS

Sanz, A., Cambra, M., De San Roman, C. et al. Preparation of additional monoclonal antibodies for detection and discrimination of potato virus Y isolates infecting potato. Potato Res 33, 365-375 (1990) (Year: 1990).*
Song et al. Preparation and detection application of monoclonal antibodies against Potato virus Y. Agric. & Life Sci. 2016,42(5):517-526 (Year: 2016).*
Song Ge et al., "Preparation and detection application of monoclonal antibodies against Potato virus Y", Journal of Zhejiang University (Agriculture & Life Sciences), 2016, 42(5): 517-526.
Cui-Ling Zhao et al., "Epitope mapping and a cocktail of monoclonal antibodies to achieve full detection coverage of potato virus Y", Plant Biotechnology Journal (2023) 21, pp. 1725-1727, Jun. 8, 2023.
Genbank, Chain G, Fab antibody fragment, heavy chain, Dec. 1, 2020.

* cited by examiner

*Primary Examiner* — Vanessa L. Ford
*Assistant Examiner* — Sandra Carter
(74) *Attorney, Agent, or Firm* — LEX IP MEISTER, PLLC

(57) ABSTRACT

The invention discloses a combination of PVY monoclonal antibodies capable of recognizing different antigenic determinants, and a use thereof, and belongs to the biotechnological field. Monoclonal antibodies N1, M1, M2, M3 and C1 obtained in the invention have specific CDRs, and are significantly different from existing reported monoclonal antibodies. The five monoclonal antibodies and a combination thereof can recognize all or most PVY isolates which have been reported, thus reducing the possibility of detection omissions; and the five monoclonal antibodies do not react with other congeneric viruses and non-congeneric viruses, thus reducing the possibility of detection errors. Therefore, the monoclonal antibodies and the combination thereof can realize accurate PVY detection.

6 Claims, 5 Drawing Sheets

Specification includes a Sequence Listing.

SEQUENCE LISTING

```
Sequence total quantity: 60
SEQ ID NO: 1              moltype = AA   length = 5
FEATURE                   Location/Qualifiers
source                    1..5
                          mol_type = protein
                          organism = synthetic construct
SEQUENCE: 1
SYGMS                                                                      5

SEQ ID NO: 2              moltype = AA   length = 17
FEATURE                   Location/Qualifiers
source                    1..17
                          mol_type = protein
                          organism = synthetic construct
SEQUENCE: 2
TINNNGGSTY YPDSVKG                                                        17

SEQ ID NO: 3              moltype = AA   length = 6
FEATURE                   Location/Qualifiers
source                    1..6
                          mol_type = protein
                          organism = synthetic construct
SEQUENCE: 3
DAAFDC                                                                     6

SEQ ID NO: 4              moltype = AA   length = 17
FEATURE                   Location/Qualifiers
source                    1..17
                          mol_type = protein
                          organism = synthetic construct
SEQUENCE: 4
KSSQSLLNSR TRKNYLA                                                        17

SEQ ID NO: 5              moltype = AA   length = 7
FEATURE                   Location/Qualifiers
source                    1..7
                          mol_type = protein
                          organism = synthetic construct
SEQUENCE: 5
WASTRES                                                                    7

SEQ ID NO: 6              moltype = AA   length = 8
FEATURE                   Location/Qualifiers
source                    1..8
                          mol_type = protein
                          organism = synthetic construct
SEQUENCE: 6
KQSYNLFT                                                                   8

SEQ ID NO: 7              moltype = AA   length = 5
FEATURE                   Location/Qualifiers
source                    1..5
                          mol_type = protein
                          organism = synthetic construct
SEQUENCE: 7
```

```
TYWMH                                                                                5

SEQ ID NO: 8            moltype = AA  length = 17
FEATURE                 Location/Qualifiers
source                  1..17
                        mol_type = protein
                        organism = synthetic construct
SEQUENCE: 8
MIKPSNSETS LNQKFKD                                                                  17

SEQ ID NO: 9            moltype = AA  length = 4
FEATURE                 Location/Qualifiers
source                  1..4
                        mol_type = protein
                        organism = synthetic construct
SEQUENCE: 9
AGDS                                                                                 4

SEQ ID NO: 10           moltype = AA  length = 16
FEATURE                 Location/Qualifiers
source                  1..16
                        mol_type = protein
                        organism = synthetic construct
SEQUENCE: 10
KSSQSLLETD GQTFLN                                                                   16

SEQ ID NO: 11           moltype = AA  length = 7
FEATURE                 Location/Qualifiers
source                  1..7
                        mol_type = protein
                        organism = synthetic construct
SEQUENCE: 11
LVSKLDS                                                                              7

SEQ ID NO: 12           moltype = AA  length = 9
FEATURE                 Location/Qualifiers
source                  1..9
                        mol_type = protein
                        organism = synthetic construct
SEQUENCE: 12
WQGTHFPLT                                                                            9

SEQ ID NO: 13           moltype = AA  length = 5
FEATURE                 Location/Qualifiers
source                  1..5
                        mol_type = protein
                        organism = synthetic construct
SEQUENCE: 13
THSMN                                                                                5

SEQ ID NO: 14           moltype = AA  length = 19
FEATURE                 Location/Qualifiers
source                  1..19
                        mol_type = protein
                        organism = synthetic construct
SEQUENCE: 14
RIRSQSNNYA TYYADSVKD                                                                19

SEQ ID NO: 15           moltype = AA  length = 8
FEATURE                 Location/Qualifiers
source                  1..8
                        mol_type = protein
                        organism = synthetic construct
SEQUENCE: 15
DYYGPFAY                                                                             8

SEQ ID NO: 16           moltype = AA  length = 16
FEATURE                 Location/Qualifiers
source                  1..16
                        mol_type = protein
                        organism = synthetic construct
SEQUENCE: 16
RSGQSLVHSN GNTYLH                                                                   16

SEQ ID NO: 17           moltype = AA  length = 7
FEATURE                 Location/Qualifiers
source                  1..7
                        mol_type = protein
                        organism = synthetic construct
```

```
SEQUENCE: 17
KVSNRFS                                                                              7

SEQ ID NO: 18          moltype = AA   length = 9
FEATURE                Location/Qualifiers
source                 1..9
                       mol_type = protein
                       organism = synthetic construct
SEQUENCE: 18
SQSTHVPWT                                                                            9

SEQ ID NO: 19          moltype = AA   length = 5
FEATURE                Location/Qualifiers
source                 1..5
                       mol_type = protein
                       organism = synthetic construct
SEQUENCE: 19
SHPLS                                                                                5

SEQ ID NO: 20          moltype = AA   length = 17
FEATURE                Location/Qualifiers
source                 1..17
                       mol_type = protein
                       organism = synthetic construct
SEQUENCE: 20
SISSGGRYTY YPDSVKG                                                                  17

SEQ ID NO: 21          moltype = AA   length = 11
FEATURE                Location/Qualifiers
source                 1..11
                       mol_type = protein
                       organism = synthetic construct
SEQUENCE: 21
RGSTATAWFA Y                                                                        11

SEQ ID NO: 22          moltype = AA   length = 15
FEATURE                Location/Qualifiers
source                 1..15
                       mol_type = protein
                       organism = synthetic construct
SEQUENCE: 22
KASQSVDYDG DSYMS                                                                    15

SEQ ID NO: 23          moltype = AA   length = 7
FEATURE                Location/Qualifiers
source                 1..7
                       mol_type = protein
                       organism = synthetic construct
SEQUENCE: 23
GASNLES                                                                              7

SEQ ID NO: 24          moltype = AA   length = 9
FEATURE                Location/Qualifiers
source                 1..9
                       mol_type = protein
                       organism = synthetic construct
SEQUENCE: 24
QQSNEDLPT                                                                            9

SEQ ID NO: 25          moltype = AA   length = 5
FEATURE                Location/Qualifiers
source                 1..5
                       mol_type = protein
                       organism = synthetic construct
SEQUENCE: 25
DYYMH                                                                                5

SEQ ID NO: 26          moltype = AA   length = 17
FEATURE                Location/Qualifiers
source                 1..17
                       mol_type = protein
                       organism = synthetic construct
SEQUENCE: 26
WIDPENGNTI YDPKFQG                                                                  17

SEQ ID NO: 27          moltype = AA   length = 5
FEATURE                Location/Qualifiers
source                 1..5
                       mol_type = protein
```

```
                                        -continued
                        organism = synthetic construct
SEQUENCE: 27
ERGAY                                                                    5

SEQ ID NO: 28           moltype = AA  length = 10
FEATURE                 Location/Qualifiers
source                  1..10
                        mol_type = protein
                        organism = synthetic construct
SEQUENCE: 28
SASSSVSYMY                                                              10

SEQ ID NO: 29           moltype = AA  length = 7
FEATURE                 Location/Qualifiers
source                  1..7
                        mol_type = protein
                        organism = synthetic construct
SEQUENCE: 29
DTSNLAS                                                                  7

SEQ ID NO: 30           moltype = AA  length = 9
FEATURE                 Location/Qualifiers
source                  1..9
                        mol_type = protein
                        organism = synthetic construct
SEQUENCE: 30
QQWSSYPLT                                                                9

SEQ ID NO: 31           moltype = AA  length = 115
FEATURE                 Location/Qualifiers
source                  1..115
                        mol_type = protein
                        organism = synthetic construct
SEQUENCE: 31
EVQLVESGGG LVQPGGSLKL SCAASGFTFS SYGMSWVRQS PDKRLEWVAT INNNGGSTYY        60
PDSVKGRFTI SRDNAKNTLY LQMSSLKSED TAVYYCARDA AFDCWGQGTT LTVSS            115

SEQ ID NO: 32           moltype = AA  length = 112
FEATURE                 Location/Qualifiers
source                  1..112
                        mol_type = protein
                        organism = synthetic construct
SEQUENCE: 32
DIVMSQSPSS LAVSAGEKVT MSCKSSQSLL NSRTRKNYLA WYQQKPGQSP KLLIYWASTR        60
ESGVPDRFTG SGSGTDFTLT ISSVQAEDLA VYYCKQSYNL FTFGSGTKLE IK               112

SEQ ID NO: 33           moltype = AA  length = 113
FEATURE                 Location/Qualifiers
source                  1..113
                        mol_type = protein
                        organism = synthetic construct
SEQUENCE: 33
QVQLQQSGPE LVRPGASVKM SCKTSGYPFS TYWMHWVKQR PGQGLEWIGM IKPSNSETSL        60
NQKFKDKATL NVDKSSNTAY MQLNSLTSED SGVYYCARAG DSWGQGTTLT VSS              113

SEQ ID NO: 34           moltype = AA  length = 112
FEATURE                 Location/Qualifiers
source                  1..112
                        mol_type = protein
                        organism = synthetic construct
SEQUENCE: 34
DVVLTQTPLT LSVTIGQPAS ISCKSSQSLL ETDGQTFLNW LLQRPGQSPK RLIYLVSKLD        60
SGVPDRFTGS GSGTDFTLKI SRVEADDLGI YYCWQGTHFP LTFGAGTKLE LK               112

SEQ ID NO: 35           moltype = AA  length = 119
FEATURE                 Location/Qualifiers
source                  1..119
                        mol_type = protein
                        organism = synthetic construct
SEQUENCE: 35
EVQLVESGGG LVQPKGSLKL SCAASDFTFN THSMNWVRQA PGKVLEWIAR IRSQSNNYAT        60
YYADSVKDRF TISRDDSQNM FYLQMNNLKT EDTAMYYCAG DYYGPFAYWG QGTLVAVSA       119

SEQ ID NO: 36           moltype = AA  length = 112
FEATURE                 Location/Qualifiers
source                  1..112
                        mol_type = protein
                        organism = synthetic construct
SEQUENCE: 36
```

```
DVLMTQTPLS  LPVSLGDQAS  ISCRSGQSLV  HSNGNTYLHW  YLQKPGQSPK  LLIYKVSNRF    60
SGVPDRFSGS  GSGTDFTLKI  SRVEAEDLGV  YFCSQSTHVP  WTFGGGTKLE  IK           112

SEQ ID NO: 37           moltype = AA   length = 120
FEATURE                 Location/Qualifiers
source                  1..120
                        mol_type = protein
                        organism = synthetic construct
SEQUENCE: 37
EVILVESGGG  LVKPGGSLRL  SCAASGFTFS  SHPLSWVRQS  PDKRLEWVAS  ISSGGRYTYY    60
PDSVKGRLTI  SRDNAKNILY  LHMNSLRSED  TAMYYCARRG  STATAWFAYW  GQGTLVTVSA   120

SEQ ID NO: 38           moltype = AA   length = 111
FEATURE                 Location/Qualifiers
source                  1..111
                        mol_type = protein
                        organism = synthetic construct
SEQUENCE: 38
DIALTQSPAS  LAVSLGQRAT  ISCKASQSVD  YDGDSYMSWY  QQKPGQPPKL  LIYGASNLES    60
GIPARFSGSG  SGTDFTLNIH  PVEEEDAATY  YCQQSNEDLP  TFGGGTKLEI  K            111

SEQ ID NO: 39           moltype = AA   length = 114
FEATURE                 Location/Qualifiers
source                  1..114
                        mol_type = protein
                        organism = synthetic construct
SEQUENCE: 39
EVQLQQSGAE  LVRPGALVKL  SCKASGFNIK  DYYMHWVKQR  PEEGLEWIGW  IDPENGNTIY    60
DPKFQGKASI  TADTSSNTVR  LQLSSLTSED  TAVYYCARER  GAYWGQGTLV  TVSA         114

SEQ ID NO: 40           moltype = AA   length = 106
FEATURE                 Location/Qualifiers
source                  1..106
                        mol_type = protein
                        organism = synthetic construct
SEQUENCE: 40
QIVLTQSPAI  MSASPGEKVT  MTCSASSSVS  YMYWFQQKPG  SSPRLLIYDT  SNLASGVPVR    60
FSGSGSGTSY  SLTISRMEAE  DAATFYCQQW  SSYPLTFGAG  TKLELK                   106

SEQ ID NO: 41           moltype = AA   length = 134
FEATURE                 Location/Qualifiers
source                  1..134
                        mol_type = protein
                        organism = synthetic construct
SEQUENCE: 41
MNLGLSFIFL  ALILKGVQCE  VQLVESGGGL  VQPGGSLKLS  CAASGFTFSS  YGMSWVRQSP    60
DKRLEWVATI  NNNGGSTYYP  DSVKGRFTIS  RDNAKNTLYL  QMSSLKSEDT  AVYYCARDAA   120
FDCWGQGTTL  TVSS                                                         134

SEQ ID NO: 42           moltype = AA   length = 132
FEATURE                 Location/Qualifiers
source                  1..132
                        mol_type = protein
                        organism = synthetic construct
SEQUENCE: 42
MDSQAQVLIL  LLLWVSGTCG  DIVMSQSPSS  LAVSAGEKVT  MSCKSSQSLL  NSRTRKNYLA    60
WYQQKPGQSP  KLLIYWASTR  ESGVPDRFTG  SGSGTDFTLT  ISSVQAEDLA  VYYCKQSYNL   120
FTFGSGTKLE  IK                                                           132

SEQ ID NO: 43           moltype = AA   length = 132
FEATURE                 Location/Qualifiers
source                  1..132
                        mol_type = protein
                        organism = synthetic construct
SEQUENCE: 43
MGWSCIILFL  AATATGVHSQ  VQLQQSGPEL  VRPGASVKMS  CKTSGYPFST  YWMHWVKQRP    60
GQGLEWIGMI  KPSNSETSLN  QKFKDKATLN  VDKSSNTAYM  QLNSLTSEDS  GVYYCARAGD   120
SWGQGTTLTV  SS                                                           132

SEQ ID NO: 44           moltype = AA   length = 131
FEATURE                 Location/Qualifiers
source                  1..131
                        mol_type = protein
                        organism = synthetic construct
SEQUENCE: 44
MSPAQFLILL  VLWIRETNGD  VVLTQTPLTL  SVTIGQPASI  SCKSSQSLLE  TDGQTFLNWL    60
LQRPGQSPKR  LIYLVSKLDS  GVPDRFTGSG  SGTDFTLKIS  RVEADDLGIY  YCWQTHFPL    120
TFGAGTKLEL  K                                                            131
```

```
SEQ ID NO: 45          moltype = AA  length = 138
FEATURE                Location/Qualifiers
source                 1..138
                       mol_type = protein
                       organism = synthetic construct
SEQUENCE: 45
MLLGLKWVFF VVFYQGVHCE VQLVESGGGL VQPKGSLKLS CAASDFTFNT HSMNWVRQAP    60
GKVLEWIARI RSQSNNYATY YADSVKDRFT ISRDDSQNMF YLQMNNLKTE DTAMYYCAGD   120
YYGPFAYWGQ GTLVAVSA                                                 138

SEQ ID NO: 46          moltype = AA  length = 131
FEATURE                Location/Qualifiers
source                 1..131
                       mol_type = protein
                       organism = synthetic construct
SEQUENCE: 46
MKLPVRLLVL MFWIPASSSD VLMTQTPLSL PVSLGDQASI SCRSGQSLVH SNGNTYLHWY    60
LQKPGQSPKL LIYKVSNRFS GVPDRFSGSG SGTDFTLKIS RVEAEDLGVY FCSQSTHVPW   120
TFGGGTKLEI K                                                        131

SEQ ID NO: 47          moltype = AA  length = 139
FEATURE                Location/Qualifiers
source                 1..139
                       mol_type = protein
                       organism = synthetic construct
SEQUENCE: 47
MNFGLSLIFL VLVLKGVQCE VILVESGGGL VKPGGSLRLS CAASGFTFSS HPLSWVRQSP    60
DKRLEWVASI SSGGRYTYYP DSVKGRLTIS RDNAKNILYL HMNSLRSEDT AMYYCARRGS   120
TATAWFAYWG QGTLVTVSA                                                139

SEQ ID NO: 48          moltype = AA  length = 131
FEATURE                Location/Qualifiers
source                 1..131
                       mol_type = protein
                       organism = synthetic construct
SEQUENCE: 48
METDTILLWV LLLWVPGSTG DIALTQSPAS LAVSLGQRAT ISCKASQSVD YDGDSYMSWY    60
QQKPGQPPKL LIYGASNLES GIPARFSGSG SGTDFTLNIH PVEEEDAATY YCQQSNEDLP   120
TFGGGTKLEI K                                                        131

SEQ ID NO: 49          moltype = AA  length = 133
FEATURE                Location/Qualifiers
source                 1..133
                       mol_type = protein
                       organism = synthetic construct
SEQUENCE: 49
MKCSWVIFFL MAVVTGVNSE VQLQQSGAEL VRPGALVKLS CKASGFNIKD YYMHWVKQRP    60
EEGLEWIGWI DPENGNTIYD PKFQGKASIT ADTSSNTVRL QLSSLTSEDT AVYYCARERG   120
AYWGQGTLVT VSA                                                      133

SEQ ID NO: 50          moltype = AA  length = 128
FEATURE                Location/Qualifiers
source                 1..128
                       mol_type = protein
                       organism = synthetic construct
SEQUENCE: 50
MDFQVQIFSF LLISASVILS RGQIVLTQSP AIMSASPGEK VTMTCSASSS VSYMYWFQQK    60
PGSSPRLLIY DTSNLASGVP VRFSGSGSGT SYSLTISRME AEDAATFYCQ QWSSYPLTFG   120
AGTKLELK                                                            128

SEQ ID NO: 51          moltype = DNA  length = 402
FEATURE                Location/Qualifiers
source                 1..402
                       mol_type = other DNA
                       organism = synthetic construct
SEQUENCE: 51
atgaacttag ggctcagctt cattttcctt gcccttattt taaaaggtgt ccagtgtgag    60
gtgcaactgg tggagtctgg gggaggctta gtgcagcctg gagggtccct gaaactctcc   120
tgtgcagcct ctggattcac tttcagtagc tatggcatgt cttgggttcg ccagagtcca   180
gacaagaggc tggaatgggt cgcaaccatt aataataatg gtggtagcac ctattatcca   240
gacagtgtga agggccgatt caccatctcc agagacaatg ccaagaacac cctgtacctg   300
caaatgagca gtctgaagtc tgaggacaca gccgtgtatt actgtgcaag agatgcggcc   360
tttgactgct ggggccaagg caccactctc acagtctcct ca                      402

SEQ ID NO: 52          moltype = DNA  length = 396
FEATURE                Location/Qualifiers
source                 1..396
                       mol_type = other DNA
                       organism = synthetic construct
```

```
SEQUENCE: 52
atggattcac aggcccaggt tcttatattg ctgctgctat gggtatctgg tacctgtggg    60
gacattgtga tgtcacagtc tccatcctcc ctggctgtgt cagcaggaga aaaggtcact   120
atgagctgca aatccagtca gagtctgctc aacagtagaa cccgaaagaa ctacttggct   180
tggtaccagc agaaaccagg gcagtctcct aaactgctga tctactgggc atccactagg   240
gaatctgggg tccctgatcg cttcacaggc agtggatctg ggacagattt cactctcacc   300
atcagcagtg tgcaggctga ggacctggca gtttattact gcaagcaatc ttataatcta   360
ttcacgttcg gctcggggac aaagttggaa ataaaa                             396

SEQ ID NO: 53          moltype = DNA  length = 396
FEATURE                Location/Qualifiers
source                 1..396
                       mol_type = other DNA
                       organism = synthetic construct
SEQUENCE: 53
atgggatgga gctgtatcat cctcttcttg gcagcaacag ctacaggtgt ccactcccag    60
gtccaactgc agcagtctgg gcctgagctg gtgaggcctg ggcttcagt gaagatgtcc    120
tgtaagactt caggctatcc cttcaagcacc tactggatgc actgggtgaa acagaggcct   180
ggacaaggcc ttgaatggat tggcatgatt aaaccttcca atagtgaaac tagtttaaat   240
cagaaattca aggacaaggc cacattgaat gtagacaaat cctccaatac agcctacatg   300
cagctcaaca gcctgacatc tgaggactct ggagtctatt actgtgcaag ggcaggggac   360
tcctgggggcc aggggcaccac tctcacagtc tcctca                           396

SEQ ID NO: 54          moltype = DNA  length = 393
FEATURE                Location/Qualifiers
source                 1..393
                       mol_type = other DNA
                       organism = synthetic construct
SEQUENCE: 54
atgagtcctg cccagttcct gattctgtta gtgctctgga ttcggggaaac caacggtgat    60
gttgtgctga cccagactcc actcactttg tcggttacca ttggacaacc agcctccatc   120
tcttgcaagt caagtcagag cctcttagaa actgatggac agacatttttt gaattggttg   180
ttacagcggc caggccagtc tccaaagcgc ctaatctatc tggtgtctaa actggactct   240
ggagtccctg acaggttcac tggcagtgga tcagggacag atttcacact gaaaatcagc   300
agagtggagg ctgacgattt gggaatttat tattgctggc aaggtacaca ttttccgctc   360
acgttcggtg ctgggaccaa gctggagctg aaa                                 393

SEQ ID NO: 55          moltype = DNA  length = 414
FEATURE                Location/Qualifiers
source                 1..414
                       mol_type = other DNA
                       organism = synthetic construct
SEQUENCE: 55
atgctgttgg ggctgaagtg ggttttcttt gttgtttttt atcaaggtgt gcattgtgag    60
gtgcagcttg ttgagtctgg tggaggattg gtgcagccta aagggtcatt gaaactctca   120
tgtgcagcct ctgatttcac cttcaatacc cactccatga actgggtccg ccaggctcca   180
ggaaaggttt tggaatggat tgctcgcata agaagtcaaa gtaataatta tgcaacatat   240
tatgccgatt cagtgaaaga caggttcacc atctccagag atgattcaca aaacatgttc   300
tatctgcaaa tgaacaactt gaaaactgag gacacagcca tgtattactg tgctggggat   360
tactacggcc cctttgctta ctggggccaa gggactctgg tcgctgtctc tgca          414

SEQ ID NO: 56          moltype = DNA  length = 393
FEATURE                Location/Qualifiers
source                 1..393
                       mol_type = other DNA
                       organism = synthetic construct
SEQUENCE: 56
atgaagttgc ctgttaggct gttggtgctg atgttctgga ttcctgcttc cagcagtgat    60
gttctgatga cccaaactcc actctccctg cctgtcagtc ttggagatca agcctccatc   120
tcttgcagat ctggtcagag ccttgtacac agtaatggaa acacctattt acattggtac   180
ctgcagaagc caggccagtc tccaaagctc ctgatctaca agtttccaa ccgattttct   240
ggggtcccag acaggttcag tggcagtgga tcagggacag atttcacact caagatcagc   300
agagtggagg ctgaggatct gggagtttat ttctgctctc aaagtacaca tgttccgtgg   360
acgttcggtg gaggcaccaa gctggaaatc aaa                                 393

SEQ ID NO: 57          moltype = DNA  length = 417
FEATURE                Location/Qualifiers
source                 1..417
                       mol_type = other DNA
                       organism = synthetic construct
SEQUENCE: 57
atgaacttcg ggctcagctt gattttcctt gtccttgttt taaaaggtgt ccagtgtgag    60
gtgatactgg tggagtctgg gggggcttta gtgaagcctg agggtccct gagactctcc   120
tgtgcagcct ctggattcac tttcagtagc catcccatgt cttgggttcg ccagagtccg   180
gacaagagge tggaatgggt cgcaagcatt agtagtggtg gtaggtacac ctactatcca   240
gacagtgtga agggccgact caccatctcc agagacaatg ccaagaacat cctgtattta   300
cacatgaaca gtctgaggtc tgaggacacg gccatgtatt actgtgcaag acggggctct   360
acggctacgg cctggtttgc ttactggggc caagggactc tggtcactgt ctctgca       417
```

```
SEQ ID NO: 58            moltype = DNA  length = 393
FEATURE                  Location/Qualifiers
source                   1..393
                         mol_type = other DNA
                         organism = synthetic construct
SEQUENCE: 58
atggagacag acacaatcct gctatgggtg ctgctgctct gggttccagg ctccactggt   60
gacattgcgc tgacccaatc tccagcttct ttggctgtgt ctctagggca gagggccacc  120
atctcctgca aggccagcca aagtgttgat tatgatggtg atagttatat gagctggtac  180
caacagaaac caggacagcc acccaaactc ctcatctatg gtgcatccaa tctagaatct  240
gggatcccag ccaggtttag tggcagtggg tctgggacag acttcaccct caacatccat  300
cctgtggagg aggaggatgc tgcaacctat tactgtcagc aaagtaatga ggatctcccg  360
acgttcggtg gaggcaccaa gctggaaatc aaa                               393

SEQ ID NO: 59            moltype = DNA  length = 399
FEATURE                  Location/Qualifiers
source                   1..399
                         mol_type = other DNA
                         organism = synthetic construct
SEQUENCE: 59
atgaaatgca gctgggtcat cttcttcctg atggcagtgg ttacaggggt caattcagag   60
gttcagctgc agcagtctgg ggctgagctt gtgaggccag gggccttagt caagttgtcc  120
tgcaaagcat ctggcttcaa cattaaagac tactatatgc actgggtgaa gcagaggcct  180
gaagagggcc tggagtggat tggatggatt gatcctgaga atggtaatac tatatatgac  240
ccgaagttcc agggcaaggc cagtataaca gcagacacat cctccaacac agtcaggctg  300
cagctcagca gcctgacatc tgaggacact gccgtctatt actgtgctag agagagggc   360
gcttactggg gccaagggac tctggtcact gtctctgca                         399

SEQ ID NO: 60            moltype = DNA  length = 384
FEATURE                  Location/Qualifiers
source                   1..384
                         mol_type = other DNA
                         organism = synthetic construct
SEQUENCE: 60
atggattttc aagtgcagat tttcagcttc ctgctaatca gtgcctcagt catactgtcc   60
agaggacaaa ttgttctcac ccagtctcca gcaatcatgt ctgcatctcc aggggagaag  120
gtcaccatga cctgcagtgc cagctcaagt gtaagttaca tgtactggtt ccagcagaag  180
ccaggatcct cccccagact cctgatttat gacacatcca acctggcttc tggagtccct  240
gttcgcttca gtggcagtgg gtctgggacc tcttactctc tcacaatcag ccgaatggag  300
gctgaagatg ctgccacttt ttactgccag cagtggagta gttacccgct cacgttcggt  360
gctgggacca agctggagct gaaa                                         384
```

COMBINATION OF PVY MONOCLONAL ANTIBODIES CAPABLE OF RECOGNIZING DIFFERENT ANTIGENIC DETERMINANTS, AND USE THEREOF

BACKGROUND OF THE INVENTION

1. Technical Field

The invention relates to the biotechnological field, in particular to a combination of PVY monoclonal antibodies capable of recognizing different antigenic determinants, and a use thereof.

2. Description of Related Art

Potato virus Y (PVY), as a representative species of potyvirus, typically infects solanaceous crops such as potato, tobacco and chilli, and severely compromises the yield and quality of crops. PVY may cause mosaic disease, vein necrosis, stalk dwarfing, tuber necrosis, ringspots, and other symptoms of potato, and mottles, mosaic disease, vein necrosis and other symptoms of tobacco, and even can result in a crop loss of 80% in severe cases. PVY may spread through aphids in a non-persistent manner, or through juice contact, and may spread through potato seeds. Timely and accurate identification of PVY makes it possible to realize the occurrence of PVY and provides a theoretical basis for monitoring, warning and comprehensive control of PVY Detection omissions or errors may lead to incorrect detection results, are disadvantageous to effective control of PVY, and severely impair safety production of crops. Commercial PVY monoclonal antibodies Mab1128, Mab1129 and Mab1130 can recognize antigenic determinants $^{25}$NLNKEK$^{30}$, $^{16}$RPEQGSIQSNP$^{26}$ and $^{51}$DAGGS$^{10}$ of coat protein (CP). However, many PVY isolates do not include these three antigenic determinants, so detection omissions will be caused when these three monoclonal antibodies are used for PVY detection. PVY polyclonal antibodies may undergo a cross reaction with other viruses of potyvirus, so detection errors will be caused when polyclonal antibodies are used for PVY detection.

It is the key to safety protection of important crops such as potato and chilli is to screen out PVY monoclonal antibodies capable of recognizing new antigenic determinants, specify the conservativeness and specificity of antigenic determinants, and combine the PVY monoclonal antibodies to realize accurate virus detection to prevent detection errors and omissions.

BRIEF SUMMARY OF THE INVENTION

In view of the prior art, the objective of the invention is to provide a combination of monoclonal antibodies capable of detecting all or most PVY isolates, and a use thereof.

To fulfill the above objective, the invention adopts the following technical solution:

In a first aspect, the invention provides a monoclonal antibody for detecting PVY, wherein the monoclonal antibody is at least one of monoclonal antibodies N1, M1, M2, M3 and C1;

The monoclonal antibody N1 comprises VHCDR1, VHCDR2 and VHCDR3 having amino acid sequences as set forth in SEQ ID NO:1-3, as well as VLCDR1, VLCDR2 and VLCDR3 having amino acid sequences as set forth in SEQ ID NO:4-6;

The monoclonal antibody M1 comprises VHCDR1, VHCDR2 and VHCDR3 having amino acid sequences as set forth in SEQ ID NO:7-9, as well as VLCDR1, VLCDR2 and VLCDR3 having amino acid sequences as set forth in SEQ ID NO:10-12;

The monoclonal antibody M2 comprises VHCDR1, VHCDR2 and VHCDR3 having amino acid sequences as set forth in SEQ ID NO:13-15, as well as VLCDR1, VLCDR2 and VLCDR3 having amino acid sequences as set forth in SEQ ID NO:16-18;

The monoclonal antibody M3 comprises VHCDR1, VHCDR2 and VHCDR3 having amino acid sequences as set forth in SEQ ID NO:19-21, as well as VLCDR1, VLCDR2 and VLCDR3 having amino acid sequences as set forth in SEQ ID NO:22-24;

The monoclonal antibody M2 comprises VHCDR1, VHCDR2 and VHCDR3 having amino acid sequences as set forth in SEQ ID NO:25-27, as well as VLCDR1, VLCDR2 and VLCDR3 having amino acid sequences as set forth in SEQ ID NO:28-30.

Further, a heavy-chain variable region of the monoclonal antibody N1 has an amino acid sequence as set forth in SEQ ID NO:31, and a light-chain variable region of the monoclonal antibody N1 has an amino acid sequence as set forth in SEQ ID NO:32; a heavy-chain variable region of the monoclonal antibody M1 has an amino acid sequence as set forth in SEQ ID NO:33, and a light-chain variable region of the monoclonal antibody M1 has an amino acid sequence as set forth in SEQ ID NO:34; a heavy-chain variable region of the monoclonal antibody M2 has an amino acid sequence as set forth in SEQ ID NO:35, and a light-chain variable region of the monoclonal antibody M2 has an amino acid sequence as set forth in SEQ ID NO:36; a heavy-chain variable region of the monoclonal antibody M3 has an amino acid sequence as set forth in SEQ ID NO:37, and a light-chain variable region of the monoclonal antibody M3 has an amino acid sequence as set forth in SEQ ID NO:38; a heavy-chain variable region of the monoclonal antibody C1 has an amino acid sequence as is set forth in SEQ ID NO:39, and a light-chain variable region of the monoclonal antibody C1 has an amino acid sequence as set forth in SEQ ID NO:40.

Further, a heavy chain of the monoclonal antibody N1 has an amino acid sequence as set forth in SEQ ID NO:41, and a light chain of the monoclonal antibody N1 has an amino acid sequence as set forth in SEQ ID NO:42; a heavy chain of the monoclonal antibody M1 has an amino acid sequence as set forth in SEQ ID NO:44, and a light chain of the monoclonal antibody M1 has an amino acid sequence as set forth in SEQ ID NO:44; a heavy chain of the monoclonal antibody M2 has an amino acid sequence as set forth in SEQ ID NO:45, and a light chain of the monoclonal antibody M2 has an amino acid sequence as set forth in SEQ ID NO:46; a heavy chain of the monoclonal antibody M3 has an amino acid sequence as set forth in SEQ ID NO:47, and a light chain of the monoclonal antibody M3 has an amino acid sequence as set forth in SEQ ID NO:48; a heavy chain of the monoclonal antibody C1 has an amino acid sequence as set forth in SEQ ID NO:49, and a light chain of the monoclonal antibody C1 has an amino acid sequence as set forth in SEQ ID NO:50.

Preferably, the monoclonal antibody is any one of combinations of monoclonal antibodies (1)-(3):

(1) a combination of the monoclonal antibody M1 and the monoclonal antibody M2;

(2) a combination of the monoclonal antibody M1 and the monoclonal antibody C1;

(3) a combination of the monoclonal antibody M2 and the monoclonal antibody C1.

In a second aspect, the invention provides a coding gene of a monoclonal antibody, comprising:

nucleotide sequences respectively coding a heavy chain and a light chain of a monoclonal antibody N1, as set forth in SEQ ID NO:51 and SEQ ID NO:52;

nucleotide sequences respectively coding a heavy chain and a light chain of a monoclonal antibody M1, as set forth in SEQ ID NO:53 and SEQ ID NO:54;

nucleotide sequences respectively coding a heavy chain and a light chain of the monoclonal antibody M2, as set forth in SEQ ID NO:55 and SEQ ID NO:56;

nucleotide sequences respectively coding a heavy chain and a light chain of a monoclonal antibody M3, as set forth in SEQ ID NO:57 and SEQ ID NO:58; or nucleotide sequences respectively coding a heavy chain and a light chain of a monoclonal antibody C1, as set forth in SEQ ID NO:59 and SEQ ID NO:60.

In a third aspect, the invention provides a use of the abovementioned monoclonal antibody in (1) or (2):

(1) detecting PVY;
(2) preparing products for detecting PVY

Preferably, the products for detecting PVY comprises, but is not limited to, an ELISA detection kit, a Western Blot detection kit, a colloid gold detection kit, and a CLIA kit.

In a fourth aspect, the invention provides an ELISA kit for detecting PVY, wherein the ELISA kit comprises the monoclonal antibody mentioned above.

The invention has the following beneficial effects:

The monoclonal antibodies N1, M1, M2, M3 and C1 and a combination thereof can recognize all or most PVY isolates which have been reported, thus reducing the possibility of detection omissions; and the five monoclonal antibodies do not react with other congeneric viruses and non-congeneric viruses, thus reducing the possibility of detection errors. Therefore, the monoclonal antibodies and the combination thereof can realize accurate PVY detection.

BRIEF DESCRIPTION OF THE SEVERAL VIEWS OF THE DRAWINGS

FIG. 3: comparing antigenic determinant sequences of monoclonal antibodies with corresponding sequences in different PVY CP amino acids.

FIG. 5: comparing antigenic determinant sequences of monoclonal antibodies with corresponding sequences in CP amino acids of different viruses of potyvirus.

DETAILED DESCRIPTION OF THE INVENTION

Figure 1:
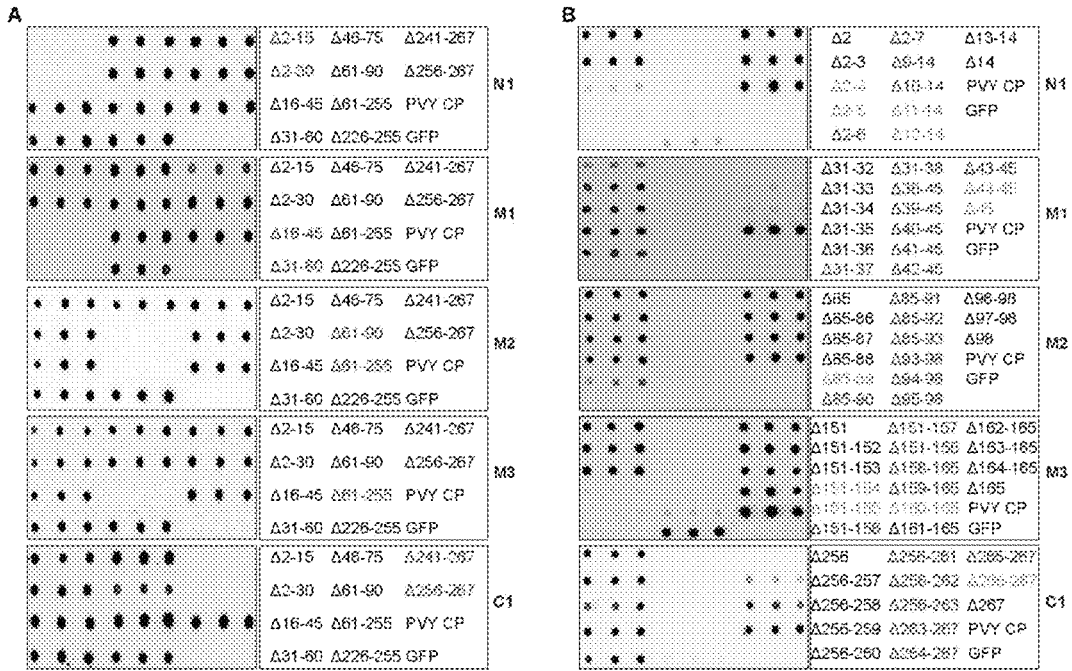
FIG. 1: screening, by dot-ELISA, monoclonal antibodies (A) capable of recognizing different regions of CP and identifying antigenic determinants of the monoclonal antibodies.

It should be pointed out that all the following details are merely illustrative and aim to provide a further description of the invention. Unless otherwise stated, all technical and scientific terms used in this specification have the same meaning as commonly understood by those ordinarily skilled in the art.

As mentioned above, detection omissions or errors of PVY may lead to incorrect detection results, are disadvantageous to effective control of PVY, and severely impair safety production of crops. As for PVY detection, PVY polyclonal antibodies can detect other viruses of potyvirus, so detection errors will be caused when polyclonal antibodies are used for PVY detection; commercial PVY monoclonal antibodies Mab1128, Mab1129 and Mab1130 can recognize antigenic determinants $^{25}$NLNKEK$^{30}$ $^{16}$RPEQGSIQSNP$^{26}$ and $^{51}$DAGGS$^{10}$ of coat protein (CP), but many PVY isolates do not include these three antigenic determinants, so detection omissions will be caused when these three monoclonal antibodies are used for PVY detection.

In view of this, in order to prevent detection omissions or errors, it is necessary to screen out PVY monoclonal antibodies capable of recognizing new antigenic determinants, specify the conservativeness and specificity of antigenic determinants, and combine the PVY monoclonal antibodies to realize accurate virus detection.

The invention provides five monoclonal antibodies N1, M1, M2, M3 and C1, antigenic determinants of which are $^{4}$TIDAGGSTK$^{12}$, $^{37}$GTSGTHTVP$^{45}$, $^{89}$QFDTWYE$^{95}$, $^{154}$PTLRQIM$^{160}$ and $^{261}$LLGVKN$^{266}$ respectively. Up to Apr. 12, 2022, complete CP amino acid sequences of 1,885 PVY isolates are recorded in NCBI totally. An analysis of the antigenic determinants indicates that N1 can recognize at least 694 isolates, M1 can recognize at least 1,853 isolates, M2 can recognize at least 1,843 isolates, M3 can recognize at least 1,848 isolates, and C1 can recognize at least 1,851 isolates; a combination of M1 and M2 can recognize all the 1,885 isolates, a combination of M1 and C1 can recognize 1,883 isolates, and a combination of M2 and C1 can recognize 1,876 isolates. The five monoclonal antibodies will not react with other congeneric viruses and non-congeneric viruses. Therefore, the monoclonal antibodies and the combination thereof provided by the invention can realize accurate detection of PVY To allow those skilled in the art to gain a better understanding of the technical solution of the application, the technical solution of the invention will be described in detail below in conjunction with specific embodiments.

All test materials used in the embodiments of the invention are conventional test materials in the art, and are commercially available. The PVY isolate used in the invention has an accession number of X977895 in NCBI. PVY monoclonal antibodies Mab1128, Mab1129 and Mab1130 are recorded in Literature Analysis of Potato virus Y Coat Protein Epitopes Recognized by Three Commercial Monoclonal Antibodies (PLoS ONE, 2014, 9(12):e115766).

Embodiment 1: Preparation of PVY Monoclonal Antibodies Capable of Recognizing Different Epitopes 1. Extraction of PVY Particles

200 g of potato leaves infected with PVY and 400 mL of 0.1 M phosphate buffer (containing 0.15% β-mercaptoethanol and 0.01M EDTA, pH=7.2) were added into a tissue crusher and stirred for 10 min. Homogenate was filtered with a gauze to remove insoluble plant tissue. An obtained solution was centrifuged at 4° C. and 8000 rpm for 30 min, and supernate was added into 1% Triton-100 and stirred at 4° C. for 3 hrs; and 6% PEG6000 and 1% NaCl were added, and stirred at 4° C. for 3 hrs. The solution was centrifuged at 4° C. and 8000 rpm for 30 min, supernate was removed, precipitate was dissolved in 40 mL of 0.1 M phosphate buffer (containing 1% Triton-100, pH=7.2) and stirred at 4° C. overnight. Then, the solution was centrifuged at 4° C. and 8000 rpm for 10 min, precipitate was removed, and supernate was added into a centrifuge tube containing a 30% sucrose cushion, and was ultra-centrifuged at 4° C. and 100,000 g for 2 hrs. Obtained precipitate was dissolved in 2 mL of 0.1M phosphate buffer, and then PVT particles were extracted.

2. Mouse Immunization

Purified PVY particles were injected into six-weeks-old female BALB/c mice every three week for three times of immunization in total, and 100 µL (25 µg) of PVY particles were injected into the mice every time. An immunogen for the first time of immunization was emulsified with the same volume of Freund's complete adjuvant, an immunogen for the second time of immunization was emulsified with the same volume of Freud's incomplete adjuvant, and an immunogen for the third time of immunization was mixed with the same volume of normal saline.

3. Preparation of Hybridoma Cell Strains

Spleen cells of the BALB/c mice and myeloma cells were mixed according to a ratio of 10:1. 50% PEG 4000 was added to the cells and blended with the cells for 3 min. Then, the cells were washed with a culture solution, then added with HAT cell culture fluid, and placed in a 96-hole cell culture plate. 7 days later, positive cells were screened out through an indirect method ELISA. The positive cells were cultured in a 24-hole plate. Monoclonal cell strains were obtained through a limiting dilution method.

4. Mass Preparation of Monoclonal Antibodies 0.5 mL of liquid paraffin was injected into the abdomen of six-weeks-old female BALB/c mice, and one week later, $10^6$ hybridoma cells were injected into the abdomen of the mice. One week later, ascites was collected in time according to abdomen expansion of the mice. Monoclonal antibodies were purified with a Protein G affinity column.

5. Screening of Monoclonal Antibodies Capable of Recognizing Different Antigenic Determinants To obtain PVY monoclonal antibodies capable of recognizing different antigenic determinants, a prokaryotic expression vector pEHISTEV-PVY CP of CP was constructed first (an expression product was PVY CP). Then, deletion mutation was carried out on pEHISTEV-PVY CP, and codon sequences of amino acids 2-15, 2-30, 16-45, 31-60, 46-75, 61-90, 61-255, 226-255, 241-267 and 256-267 were deleted to obtain plasmids of expressible deletion mutants CPΔ2-15, CPΔ2-30, CPΔ16-45, CPΔ31-60, CPΔ46-75, CPΔ61-90, CPΔ61-255, CPΔ226-255, CPΔ241-267 and CPΔ256-267. pEHISTEV-GFP is negative control, and can be expressed as GFP.

dot-ELISA was carried out on the purified monoclonal antibodies, PVY CP and mutants of the PVY CP as follows:

Potato samples infected with PVY were diluted with a PBS buffer according to a weight ratio of 1:40, 2 µL of diluted sample protein was dropwise added on a nitrocellulose membrane (NC membrane), and then the NC membrane was aired at room temperature. The NC membrane was placed in 10 mL of blocking buffer, and was blocked in a table concentrator at room temperature for 2 h or was blocked at 4° C. overnight. The blocking buffer on the NC membrane is washed away, then the NC membrane was placed in skim milk powder containing the purified monoclonal antibodies (primary antibodies) and prepared from TBST, and incubated in the table concentrator at room temperature for 1 h or incubated in a refrigerator at 4° C. overnight, and then the NC membrane was washed with 10 mL of TBST for three times, 10 min each time. The NC membrane was placed in a buffer containing IgG (Sigma-Aldrich) second antibodies labelled by horseradish peroxidase, and incubated in the table concentrator at room temperature for 1 h; the NC membrane was washed with 10 mL of TBST twice, each 10 min, and then washed with TBS for 10 min. A developing agent was added to the NC membrane, and then the MC membrane was placed on a chemiluminescence instrument to be developed and photographed.

Five monoclonal antibodies N1, M1, M2, M3 and C1 capable of recognizing different areas were screened out according to mutants recognized by the monoclonal antibodies. Wherein, N1 did not react with CPΔ2-15 and CPΔ2-30, M1 did not react with CPΔ16-45 and CPΔ31-60, M2 did not react with CPΔ61-90 and CPΔ61-255, M3 did not react with CPΔ61-255, and C1 did not react with CPΔ241-267 and CPΔ256-267 (FIG. 1A).

6. Identification of Antigenic Determinants of the Five PVY Monoclonal Antibodies Key amino acids were identified according to reaction results to figure out the minimum determinant capable of being recognized by the antibodies. dot-ELISA results indicate that N1 can recognize amino acids 2-15, M1 can recognize amino acids 31-45, M2 can recognize amino acids 61-90, M3 can recognize amino acids 90-226, and C1 can recognize amino acids 256-267. To narrow the range of the regions of antigenic determinants of M2 and M3, a further deletion mutation analysis was carried out to conclude that the antigenic determinant of M2 corresponds to amino acids 85-98, and the antigenic determinant of M3 corresponds to amino acids 151-165.

To identify specific amino acid sites of a PVY CP antigenic determinant recognized by the monoclonal antibody N1, deletion mutation was carried out on amino acids 2-14 of pEHISTEV-PVY CP to obtain plasmids of expressible deletion mutants CPΔ2, CPΔ2-3, CPΔ2-4, CPΔ2-5, CPΔ2-6, CPΔ2-7, CPΔ9-14, CPΔ10-14, CPΔ11-14, CPΔ12-14, CPΔ13-14 and CPΔ14.

dot-ELISA was carried out on the mutants by N1. Results show that N1 reacts with CPΔ2-3 and CPΔ13-14, slightly reacts with CPΔ2-4, CPΔ2-5, CPΔ11-14 and CPΔ12-14, and does not react with CPΔ2-6, CPΔ2-7, CPΔ9-14 and CPΔ10-14 (FIG. 1*i*), indicating that the antigenic determinant recognized by N1 corresponds to amino acids 4-12 TIDAGG-STK of the PVY CP.

According to the range of amino acids recognized by the other four antibodies, deletion mutation was carried out in the similar way to obtain corresponding plasmids. dot-ELISA results show that the monoclonal antibody M1 react with CPΔ31-36, slightly reacts with CPΔ44-45 and CPΔ45, and does not react with CPΔ31-37, CPΔ31-38, CPΔ38-45, CPΔ39-45, CPΔ40-45, CPΔ41-45, CPΔ42-45 and CPΔ43-45 (FIG. 1*i*), indicating that the antigenic determinant recognized by M1 corresponds to amino acids 37-45 GTSGTH-TVP of the PVY CP.

The monoclonal antibody M2 reacts with CPΔ85-88 and CPΔ96-98, slightly reacts with CPΔ85-89, and does not react with CPΔ85-90, CPΔ85-91, CPΔ85-92, CPΔ85-93, CPΔ93-98, CPΔ94-98 and CPΔ95-98 (FIG. 1), indicating that the antigenic determinant recognized by M1 corresponds to amino acids 89-95 QFDTWYE of the PVY CP.

The monoclonal antibody M3 reacts with CPΔ151-153 and CPΔ161-165, slightly reacts with CPΔ151-154, CPΔ151-155 and CPΔ160-165, and does not react with CPΔ151-156, CPΔ151-157, CPΔ151-158, CPΔ158-165 and CPΔ159-165 (FIG. 1i), indicating that the antigenic determinant recognized by N1 corresponds to amino acids 154-160 PTLRQIM of the PVY CP.

The monoclonal antibody C1 reacts with CPΔ256-260 and CPΔ267, slightly reacts with CPΔ266-267, and does not react with CPΔ256-261, CPΔ256-262, CPΔ256-263, CPΔ263-267, CPΔ264-267 and CPΔ265-267 (FIG. 1i), indicating that the antigenic determinant recognized by C1 corresponds to amino acids 261-266 LLGVKN of the PVY CP.

7. Identification of the Subtype and Valence of the Five PVY Monoclonal Antibodies The subtype and subclass of the five monoclonal antibodies MAb N1, M1, M2, M3 and C1 are identified as IgG1, IgG1, IgG1, IgG1 and IgG2b, with a light chain kappa (Table 1). By indirect ELISA detection, the valence of the five monoclonal antibodies can reach 1:243000 (Table 1).

TABLE 1

Subtype and valence of monoclonal antibodies

| MAbs | Isotype | Titer |
|---|---|---|
| N1 | IgG1, κ chain | 1:243000 |
| M1 | IgG1, κ chain | 1:243000 |
| M2 | IgG1, κ chain | 1:243000 |
| M3 | IgG1, κ chain | 1:243000 |
| C1 | IgG2b, κ chain | 1:243000 |

Embodiment 2: Detection of PVY isolate CP that cannot be recognized by MAb1128, MAb1129 and MAb1130 with MAbs N1, M1, M2, M3 and C1

Figure 2:
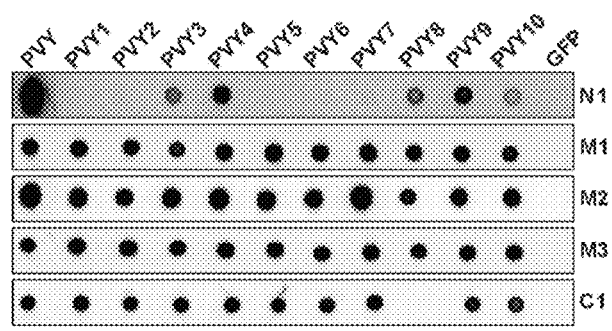
FIG. 2: analyzing, by dot-ELISA, the recognition of monoclonal antibodies to different PVY isolates.

10 PVY isolate CP sequences not including antigenic determinants that can be recognized by MAb1128, MAb1129 and MAb1130 were synthesized. The serial numbers of 10 PVY isolates in NCBI were CAA66472, CAA48304, ABY78978, CAA48306, CAA94183, AAL35616, ABQ53158, CAE51190, CAA32356, CAA48302 and CAA94184 respectively.

dot-ELISA results indicate that N1 cannot recognize isolates PVY1, PVY2, PVY5 and PVY6, M1, M2 and M3 can recognize all the 10 isolates, and C1 cannot recognize the isolate PVY8 (FIG. 2).

Figure 3:
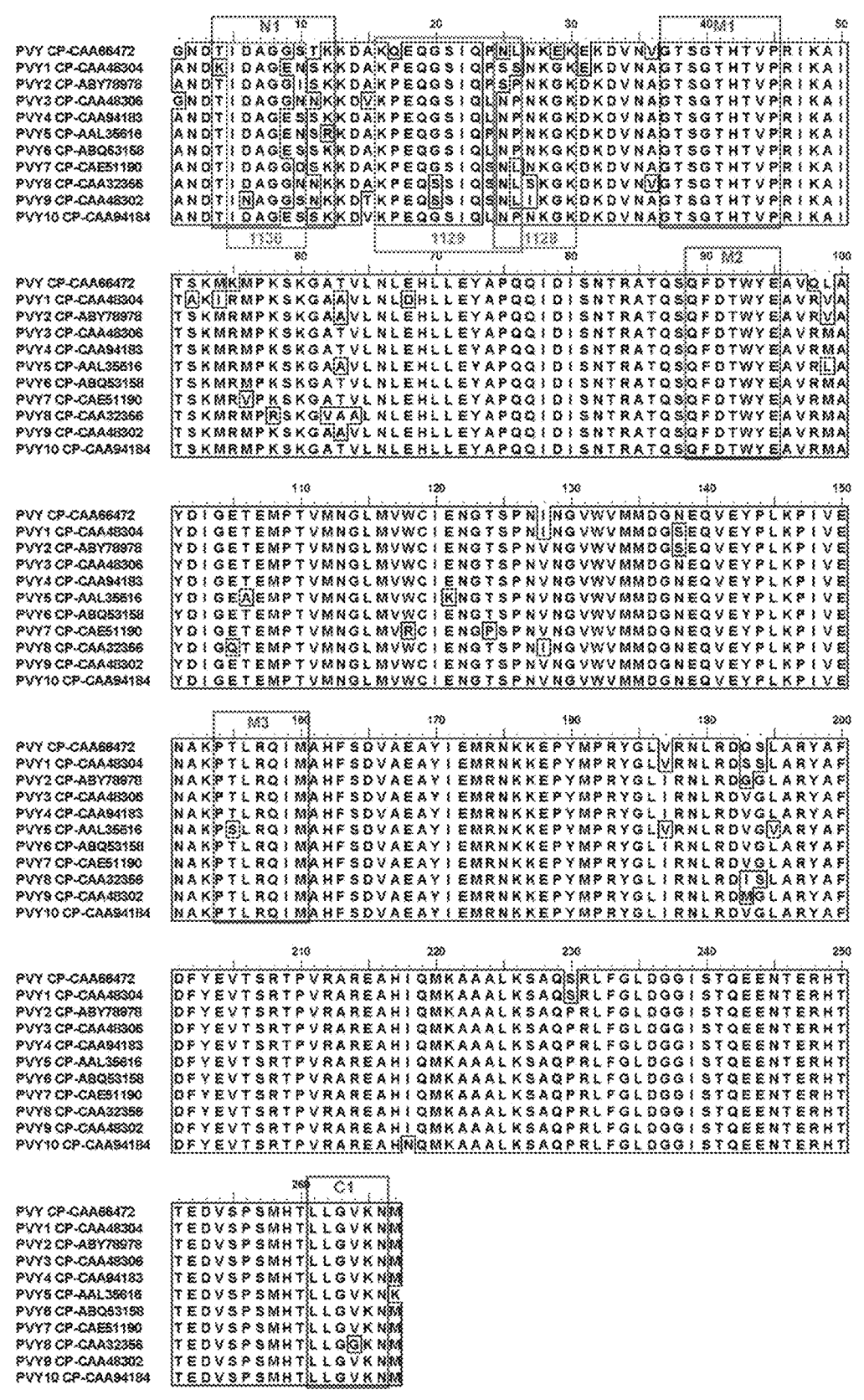

It is found by a further sequence analysis that the 10 PVY isolate CP sequences do not include the antigenic determinant recognized by N1 and include antigenic determinants recognized by M1 and M2, the other 9 isolate CP sequences except PVY5 include the antigenic determinant recognized by M3, and the other 9 isolate CP sequences except PVY8 include the antigenic determinant recognized by C1 (FIG. 3), indicating that M1, M2, M3 and C1 can recognize all or most isolates that cannot be recognized by MAb1128, MAb1129 and MAb1130.

Embodiment 3: Specificity analysis of the PVY monoclonal antibodies

Specificity analysis was carried out on the five monoclonal antibodies N1, M1, M2, M3 and C1 screened out in Embodiment 1 specifically as follows:

The five monoclonal antibodies were used for detecting, by means of dot blot, prokaryotic expression CPs of turnip mosaic virus (TuMV) (genus Potyvirus), tobacco vein banding mosaic virus (TVBMV) (genus Potyvirus), potato virus X (PVX) (genus Potexvirus), tobacco mosaic virus (TMV) (genus Tobamovirus), tomato mosaic virus (ToMV) (genus Tobamovirus), tomato mottle mosaic virus (ToMMV) (genus Tobamovirus), tomato brown rugose fruit virus (ToMMV) (genus Tobamovirus), chilli ringspot virus (ChiRSV) (genus Potyvirus), chilli mottle virus (PepMoV) (genus Potyvirus), potato virus A (PVA) (genus Potyvirus), chilliveinal mottle virus (PVMV) (genus Potyvirus), tobacco vein mottling virus (TVMV) (genus Potyvirus), potato virus M (PVM) (genus Carlavirus), potato virus M (PVM) (genus Carlavirus), and potato virus S (PVS) (genus Carlavirus).

Figure 4:
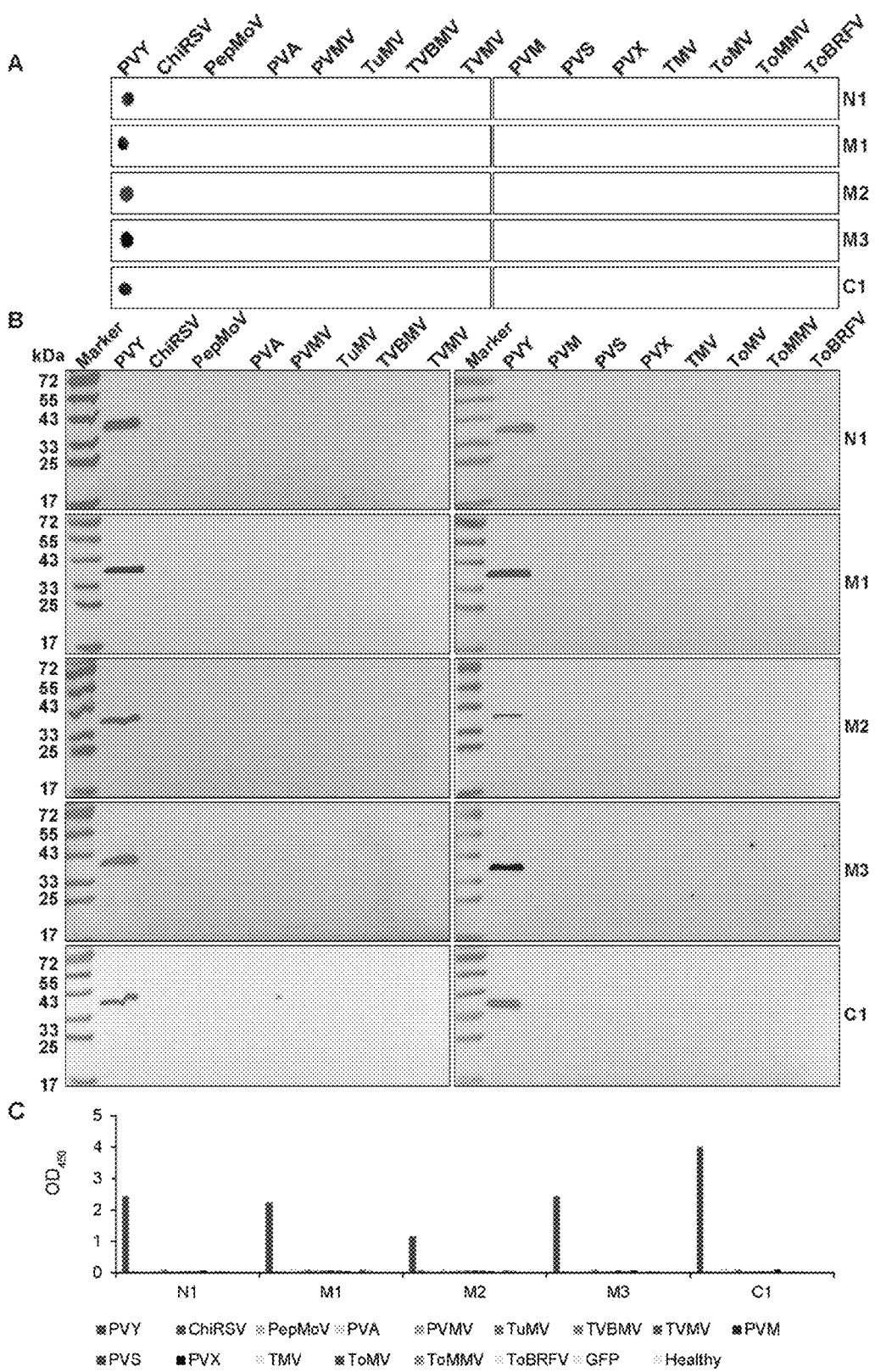
FIG. 4: analyzing the specificity of monoclonal antibodies to different viruses.
Figure 5:
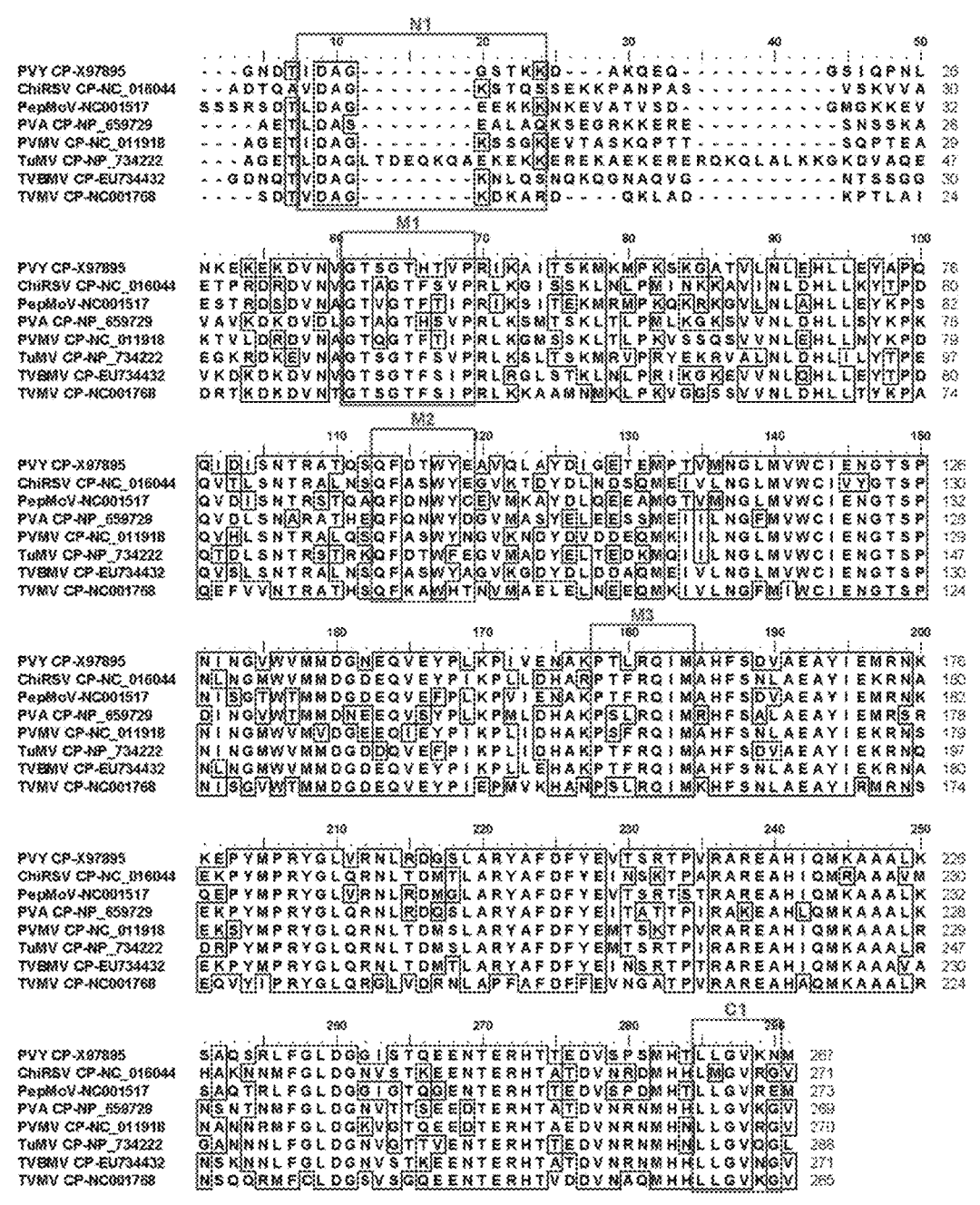

Dot blot results show that the five monoclonal antibodies can recognize PVY and will not undergo a cross reaction with the other 14 viruses or CPs, thus having high specificity (FIG. 4A). Western blot and ELISA also further prove that the specificity of the five monoclonal antibodies (FIG. 4B and FIG. 4C). It is found, by analyzing the CP sequences of the eight viruses of Potyvirus, that the antigenic determinant sequences of the five monoclonal antibodies are not 100% consistent with the sequences of the other seven viruses (FIG. 5), indicating that the five monoclonal antibodies can specially recognize antigenic determinant sequences on the PVY CP.

Embodiment 4: Sensitivity Analysis of the PVY Monoclonal Antibodies

Sensitivity analysis was carried out on the five monoclonal antibodies N1, M1, M2, M3 and C1 screened out in Embodiment 1 respectively through dot-ELISA.

Figure 6:
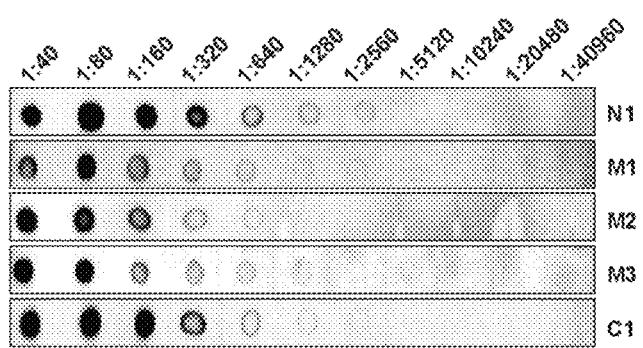
FIG. 6: analyzing, by dot-ELISA, the antigen sensitivity of monoclonal antibodies.

First, juice infected with PVY was diluted. Then, dot-ELISA was carried out in the same way as Embodiment 1. Results indicate that N1 can detect the juice diluted by 10,240 times, M1 can detect the juice diluted by 5,120 times, M2 can detect the juice diluted by 640 times, M3 can detect the juice diluted by 5,120 times, and C1 can detect the juice diluted by 5,120 times (FIG. 6).

Embodiment 5: Analysis of PVY Isolate Coverage of the PVY Monoclonal Antibodies

Up to Apr. 12, 2022, the complete CP amino acid sequences of 1,885 PVY isolates are recorded in NCBI totally. It was found, by sequence analysis, that 694 isolates include the antigenic determinant sequence TIDAGGSTK recognized by N1, 1,853 isolates include the antigenic determinant sequence GTSGTHTVP recognized by M1, 1,843 isolates include the antigenic determinant sequence QFDTWYE recognized by M2, 1,848 isolates include the antigenic determinant sequence PTLRQIM recognized by M3, and 1,851 isolates include the antigenic determinant sequence LLGVKN recognized by C1. The monoclonal antibodies M1, M2, M3 and C1 can detect 11.35%, 10.82%, 11.09% and 11.25% more isolates than MAb1130 (Table 2).

TABLE 2

PVY isolate coverage of monoclonal antibodies

| MAbs | The number (percentage) of isolates without the epitope among 1885 isolates | The number (percentage) of isolates with the epitope among 1885 isolates |
|---|---|---|
| 1128 | 1146 (60.80%) | 739 (39.20%) |
| 1129 | 1238 (65.68%) | 647 (34.32%) |
| 1130 | 246 (13.05%) | 1639 (86.95%) |
| N1 | 1191 (63.18%) | 694 (36.82%) |
| M1 | 32 (1.70%) | 1853 (98.3%) |
| M2 | 42 (2.23%) | 1843 (97.77%) |
| M3 | 37 (1.96%) | 1848 (98.04%) |
| C1 | 34 (1.80%) | 1851 (98.20%) |

The antigenic determinant (PTLRQIM) recognized by the monoclonal antibody M3 corresponds to the sequence PSLRQIM in the PVY5 isolate CP, and also corresponds to the sequence PSLRQIM in TVMV and PVA CP. As analyzed in Embodiment 2 and Embodiment 3, although M3 can recognize PVY5, it cannot recognize TVMV and PVA, so M3 is not the optimal antibody, and will not be taken into account by preferred PVY monoclonal antibody combinations. In addition, the monoclonal antibody N1 can only recognize a few isolates, and thus will not be taken into account either. The 1,885 PVY isolates are numbered from 1-1885, and it can be found, by analyzing the antigenic determinants of the PVY isolates, that themonoclonal antibody M1 cannot recognize 32 PVY isolates, the monoclonal antibody M2 cannot recognize 42 PVY isolates, and the monoclonal antibody C1 cannot recognize 34 PVY isolates. The serial numbers of the isolates are specially shown in Table 3. It is found, by analyzing the serial numbers of the PVY isolates not including the antigenic determinants recognized by MAb M1, M20r C1, that a combination of the monoclonal antibodies M1 and M2 can recognize all the 1,885 PVY isolates, a combination of the monoclonal antibodies M1 and C1 can recognize the other 1,883 PVY isolates except 1107(NCBIaccession number in NCBI. AMW64585.1) and 1344 (AYA57928.1), a combination of the monoclonal antibodies M2 and C1 can recognize the other 1,876 PVY isolates except 380 (AEF59038.1), 381 (AEF59039.1), 788 (AGX27987.1), 789 (AGX27988.1), 790 (AGX27989.1), 991 (AIL50122.1), 992 (AIL50123.1), 993 (AIL50124.1) and 994 (AIL50125.1).

Table 3 Serial numbers of isolates that cannot be recognized by monoclonal antibodies M1, M2 and C1

TABLE 3

Serial numbers of isolates that cannot be recognized by monoclonal antibodies M1, M2 and C1

| M1 | 76 | 83 | 142 | 201 | 250 | 303 | 371 | 523 | 582 | 619 | 620 | 621 |
|---|---|---|---|---|---|---|---|---|---|---|---|---|
|  | 799 | 895 | 909 | 913 | 956 | 1032 | 1035 | _1107_ | 1113 | 1136 | 1189 | _1344_ |
|  | 1350 | 1429 | 1496 | 1500 | 1520 | 1555 | 1563 | 1613 |  |  |  |  |
| M2 | 67 | 89 | 380 | 381 | 420 | 448 | 449 | 541 | 556 | 581 | 584 | 609 |
|  | 612 | 654 | 655 | 656 | 657 | 658 | 724 | 787 | 788 | 789 | 790 | 806 |
|  | 809 | 920 | 991 | 992 | 993 | 994 | 1024 | 1067 | 1097 | 1394 | 1476 | 1492 |
|  | 1525 | 1526 | 1537 | 1560 | 1645 | 1714 |  |  |  |  |  |  |
| C1 | 206 | 293 | 377 | 379 | 380 | 381 | 432 | 471 | 622 | 788 | 789 | 790 |
|  | 991 | 992 | 993 | 994 | 1027 | 1064 | _1107_ | 1270 | 1274 | 1341 | _1344_ | 1421 |
|  | 1424 | 1425 | 1463 | 1523 | 1527 | 1567 | 1719 | 1794 | 1795 | 1798 |  |  |

Note:
bold and italic serial numbers in Table 3 are serial numbers of PVY isolates that cannot be recognized by the combination of the monoclonal antibodies M1 and C1.
Bold serial numbers in Table 3 are serial numbers of PVY isolates that cannot be recognized by the combination of M2 and C1.

Note: b old and italic serial numbers in Table 3 are serial numbers of PVY isolates that cannot be recognized by the combination of the monoclonal antibodies M1 and C1. Bold serial numbers in Table 3 are serial numbers of PVY isolates that cannot be recognized by the combination of M2 and C1.

Embodiment 6: Sequence and Structure Analysis of the PVY Monoclonal Antibodies

Sequence and structure analysis was further carried out on the five monoclonal antibodies N1, M1, M2, M3 and C1 screened out in Embodiment 1, wherein:

The monoclonal antibodies comprise: a heavy chain and a light chain. Specifically:

An amino acid sequence of the heavy chain of the monoclonal antibody N1;

(SEQ ID NO: 40)
MNLGLSFIFLALILKGVQCEVQLVESGGGLVQPGGSLKLSCAASGFTFS

_SYGMS_WVRQSPDKRLEWVA_TINNNGGSTYYPDSVKG_RFTISRDNAKN

TLYLQMSSLKSEDTAVYYCAR_DAAFDC_WGQGTTLTVSS

Note: the shadow area is a heavy-chain variable region; the italic, bold and underlined areas are CDRs, which are VHCDR1, VHCDR2 and VHCDR3 in sequence.

An amino acid sequence of the light chain of the monoclonal antibody N1;

(SEQ ID NO: 42)
MDSQAQVLILLLLWVSGTCGDIVMSQSPSSLAVSAGEKVTMSC_K_

_SSQSLLNSRTRKNYLA_WYQQKPGQSPKLLIY_WASTRES_GVPD

RFTGSGSGTDFTLTISSVQAEDLAVYYC_KQSYNLFT_FGSGTKL

EIK

Note: the shadow area is a light-chain variable region; the italic, bold and underlined areas are CDRs, which are VLCDR1, VLCDR2 and VLCDR3 in sequence.

A nucleotide sequence for coding the heavy chain of the monoclonal antibody N1;

(SEQ ID NO: 51)
ATGAACTTAGGGCTCAGCTTCATTTTCCTTGCCCTTATTTTAAAAGGTG

TCCAGTGTGAGGTGCAACTGGTGGAGTCTGGGGGAGGCTTAGTGCAGCCT

-continued

GGAGGGTCCCTGAAACTCTCCTGTGCAGCCTCTGGATTCACTTTCAGTAG

CTATGGCATGTCTTGGGTTCGCCAGAGTCCAGACAAGAGGCTGGAATGGG

TCGCAACCATTAATAATAATGGTGGTAGCACCTATTATCCAGACAGTGTG

AAGGGCCGATTCACCATCTCCAGAGACAATGCCAAGAACACCCTGTACCT

GCAAATGAGCAGTCTGAAGTCTGAGGACACAGCCGTGTATTACTGTGCAA

GAGATGCGGCCTTTGACTGCTGGGGCCAAGGCACCACTCTCACAGTCTCC

TCA

Note: the shadow area is a coding sequence of the heavy-chain variable region.

A nucleotide sequence for coding the light chain of the monoclonal antibody N1;

(SEQ ID NO: 52)
ATGGATTCACAGGCCCAGGTTCTTATATTGCTGCTGCTATGGGTATCTG

GTACCTGTGGGGACATTGTGATGTCACAGTCTCCATCCTCCCTGGCTGTG

TCAGCAGGAGAGAAGGTCACTATGAGCTGCAAATCCAGTCAGAGTCTGCT

CAACAGTAGAACCCGAAAGAACTACTTGGCTTGGTACCAGCAGAAACCAG

GGCAGTCTCCTAAACTGCTGATCTACTGGGCATCCACTAGGGAATCTGGG

GTCCCTGATCGCTTCACAGGCAGTGGATCTGGGACAGATTTCACTCTCAC

CATCAGCAGTGTGCAGGCTGAGGACCTGGCAGTTTATTACTGCAAGCAAT

CTTATAATCTATTCACGTTCGGCTCGGGGACAAAGTTGGAAATAAAA

Note: the shadow area is a coding sequence of the light-chain variable region.

An amino acid sequence of the heavy chain of the monoclonal antibody M1;

(SEQ ID NO: 43)
MGWSCIILFLAATATGVHSQVQLQQSGPELVRPGASVKMSCKTSGYPFS

*TYWMH*WVKQRPGQGLEWIG*MIKPSNSETSLNQKFKD*KATLNVDKS

SNTAYMQLNSLTSEDSGVYYCAR*AGDS*WGQGTTLTVSS

Note: the shadow area is a heavy-chain variable region; the italic, bold and underlined areas are CDRs, which are VHCDR1, VHCDR2 and VHCDR3 in sequence.

An amino acid sequence of the light chain of the monoclonal antibody M1;

(SEQ ID NO: 44)
MSPAQFLILLVLWIRETNGDVVLTQTPLTLSVTIGQPASISC

*KSSQSLLETDGQTFLN*WLLQRPGQSPKRLIY*LVSKLDS*

GVPDRFTGSGSGTDFTLKISRVEADDLGIYYC*WQGTHFPLT*

FGAGTKLELK

Note: the shadow area is a light-chain variable region; the italic, bold and underlined areas are CDRs, which are VLCDR1, VLCDR2 and VLCDR3 in sequence.

A nucleotide sequence for coding the heavy chain of the monoclonal antibody M1;

(SEQ ID NO: 53)
ATGGGATGGAGCTGTATCATCCTCTTCTTGGCAGCAACAGCTACAGGT

GTCCACTCCCAGGTCCAACTGCAGCAGTCTGGGCCTGAGCTGGTGAGGCC

TGGGGCTTCAGTGAAGATGTCCTGTAAGACTTCAGGCTATCCCTTCAGCA

CCTACTGGATGCACTGGGTGAAACAGAGGCCTGGACAAGGCCTTGAATGG

ATTGGCATGATTAAACCTTCCAATAGTGAAACTAGTTTAAATCAGAAATT

CAAGGACAAGGCCACATTGAATGTAGACAAATCCTCCAATACAGCCTACA

TGCAGCTCAACAGCCTGACATCTGAGGACTCTGGAGTCTATTACTGTGCA

AGGGCAGGGGACTCCTGGGGCCAGGGCACCACTCTCACAGTCTCCTCA

Note: the shadow area is a coding sequence of the heavy-chain variable region.

A nucleotide sequence for coding the light chain of the monoclonal antibody M1;

(SEQ ID NO: 54)
ATGAGTCCTGCCCAGTTCCTGATTCTGTTAGTGCTCTGGATTCGGGAA

ACCAACGGTGATGTTGTGCTGACCCAGACTCCACTCACTTTGTCGGTTAC

CATTGGACAACCAGCCTCCATCTCTTGCAAGTCAAGTCAGAGCCTCTTAG

AAACTGATGGACAGACATTTTTGAATTGGTTGTTACAGCGGCCAGGCCAG

TCTCCAAAGCGCCTAATCTATCTGGTGTCTAAACTGGACTCTGGAGTCCC

TGACAGGTTCACTGGCAGTGGATCAGGGACAGATTTCACACTGAAAATCA

GCAGAGTGGAGGCTGACGATTTGGGAATTTATTATTGCTGGCAAGGTACA

CATTTTCCGCTCACGTTCGGTGCTGGGACCAAGCTGGAGCTGAAA

Note: the shadow area is a coding sequence of the light-chain variable region.

An amino acid sequence of the heavy chain of the monoclonal antibody M2;

(SEQ ID NO: 45)
MLLGLKWVFFVVFYQGVHCEVOLVESGGGLVQPKGSLKLSCAASDFTF

N*THSMN*WVRQAPGKVLEWIA*RIRSQSNNYATYYADSVKD*RFTISRD

DSQNMFYLQMNNLKTEDTAMYYCAG*DYYGPFAY*WGQGTLVAVSA

Note: the shadow area is a heavy-chain variable region; the italic, bold and underlined areas are CDRs, which are VHCDR1, VHCDR2 and VHCDR3 in sequence.

An amino acid sequence of the light chain of the monoclonal antibody M2;

(SEQ ID NO: 46)
MKLPVRLLVLMFWIPASSSDVLMTQTPLSLPVSLGDQASISC*RSG*

*QSLVHSNGNTYLH*WYLQKPGQSPKLLIY*KVSNRFS*GVPDRFSGS

GSGTDFTLKISRVEAEDLGVYFC*SQSTHVPWT*FGGGTKLEIK

Note: the shadow area is a light-chain variable region; the italic, bold and underlined areas are CDRs, which are VLCDR1, VLCDR2 and VLCDR3 in sequence.

A nucleotide sequence for coding the heavy chain of the monoclonal antibody M2;

(SEQ ID NO: 55)
ATGCTGTTGGGGCTGAAGTGGGTTTTCTTTGTTGTTTTTTATCAAGGTG

TGCATTGTGAGGTGCAGCTTGTTGAGTCTGGTGGAGGATTGGTGCAGCC

TAAAGGGTCATTGAAACTCTCATGTGCAGCCTCTGATTTCACCTTCAAT

ACCCACTCCATGAACTGGGTCCGCCAGGCTCCAGGAAAGGTTTTGGAAT

GGATTGCTCGCATAAGAAGTCAAAGTAATAATTATGCAACATATTATGC

CGATTCAGTGAAAGACAGGTTCACCATCTCCAGAGATGATTCACAAAAC

ATGTTCTATCTGCAAATGAACAACTTGAAAACTGAGGACACAGCCATGT

ATTACTGTGCTGGGGATTACTACGGCCCCTTTGCTTACTGGGGCCAAGG

GACTCTGGTCGCTGTCTCTGCA

Note: the shadow area is a coding sequence of the heavy-chain variable region.

A nucleotide sequence for coding the light chain of the monoclonal antibody M2;

(SEQ ID NO: 56)
ATGAAGTTGCCTGTTAGGCTGTTGGTGCTGATGTTCTGGATTCCTGCTT

CCAGCAGTGATGTTCTGATGACCCAAACTCCACTCTCCCTGCCTGTCAG

TCTTGGAGATCAAGCCTCCATCTCTTGCAGATCTGGTCAGAGCCTTGTA

CACAGTAATGGAAACACCTATTTACATTGGTACCTGCAGAAGCCAGGCC

AGTCTCCAAAGCTCCTGATCTACAAAGTTTCCAACCGATTTTCTGGGGT

CCCAGACAGGTTCAGTGGCAGTGGATCAGGGACAGATTTCACACTCAAG

ATCAGCAGAGTGGAGGCTGAGGATCTGGGAGTTTATTTCTGCTCTCAAA

GTACACATGTTCCGTGGACGTTCGGTGGAGGCACCAAGCTGGAAATCAA

A

Note: the shadow area is a coding sequence of the light-chain variable region.

An amino acid sequence of the heavy chain of the monoclonal antibody M3;

(SEQ ID NO: 47)
MNFGLSLIFLVLVLKGVQCEVILVESGGGLVKPGGSLRLSCAASGFTFS

*SHPLSWVRQSPDKRLEWVSISSGGRYTYYPDSVKGRLTISRDNAKNI*

LYLHMNSLRSEDTAMYYCAR*RGSTATAWFAY*WGQGTLVTVSA

Note: the shadow area is a heavy-chain variable region; the italic, bold and underlined areas are CDRs, which are VHCDR1, VHCDR2 and VHCDR3 in sequence.

An amino acid sequence of the light chain of the monoclonal antibody M3;

(SEQ ID NO: 48)
METDTILLWVLLLWVPGSTGDIALTQSPASLAVSLGQRATISC*KAS*

*QSVDYDGDSYMS*WYQQKPGQPPKLLIY*GASNLES*GIPARFSGSGS

GTDFTLNIHPVEEEDAATYYC*QQSNEDLPT*FGGGTKLEIK

Note: the shadow area is a light-chain variable region; the italic, bold and underlined areas are CDRs, which are VLCDR1, VLCDR2 and VLCDR3 in sequence.

A nucleotide sequence for coding the heavy chain of the monoclonal antibody M3;

(SEQ ID NO: 57)
ATGAACTTCGGGCTCAGCTTGATTTTCCTTGTCCTTGTTTTAAAAGGTG

TCCAGTGTGAGGTGATACTGGTGGAGTCTGGGGGGGGCTTAGTGAAGCC

TGGAGGGTCCCTGAGACTCTCCTGTGCAGCCTCTGGATTCACTTTCCAG

TAGCATCCCTTGTCTTGGGTTCGCCAGAGTCCGGACAAGAGGCTGGAAT

GGGTCGCAAGCATTAGTAGTGGTGGTAGGTACACCTACTATCCAGACAG

TGTGAAGGGGCGACTCACCATCTCCAGAGACAATGCCAAGAACATCCTG

TATTTACACATGAACAGTCTGAGGTCTGAGGACACGGCCATGTATTACT

GTGCAAGACGGGGCTCTACGGCTACGGCCTGGTTTGCTTACTGGGGCCA

AGGGACTCTGGTCACTGTCTCTGCA

Note: the shadow area is a coding sequence of the heavy-chain variable region.

A nucleotide sequence for coding the light chain of the monoclonal antibody M3;

(SEQ ID NO: 58)
ATGGAGACAGACACAATCCTGCTATGGGTGCTGCTGCTCTGGGTTCCA

GGCTCCACTGGTGACATTGCGCTGACCCAATCTCCAGCTTCTTTGGCTG

TGTCTCTAGGGCAGAGGGCCACCATCTCCTGCAAGGCCAGCCAAAGTGT

TGATTATGATGGTGATAGTTATATGAGCTGGTACCAACAGAAACCAGGA

CAGCCACCCAAACTCCTCATCTATGGTGCATCCAATCTAGAATCTGGGA

TCCCAGCCAGGTTTAGTGGCAGTGGGTCTGGGACAGACTTCACCCTCAA

CATCCATCCTGTGGAGGAGGAGGATGCTGCAACCTATTACTGTCAGCAA

AGTAATGAGGATCTCCCGACGTTCGGTGGAGGCACCAAGCTGGAAATCA

AA

Note: the shadow area is a coding sequence of the light-chain variable region.

An amino acid sequence of the heavy chain of the monoclonal antibody C1;

(SEQ ID NO: 49)
MKCSWVIFFLMAVVTGVNSEVQLQQSGAELVRPGALVKLSCKASGFNIK

*DYYMH*WVKQRPEEGLEWIG*WIDPENGNTIYDPKFQG*KASITADTSSN

TVRLQLSSLTSEDTAVYYCAR*ERGAY*WGQGTLVTVSA

Note: the shadow area is a heavy-chain variable region; the italic, bold and underlined areas are CDRs, which are VHCDR1, VHCDR2 and VHCDR3 in sequence.

An amino acid sequence of the light chain of the monoclonal antibody C1;

(SEQ ID NO: 50)
MDFQVQIFSFLLISASVILSRGQIVLTQSPAIMSASPGEKVTMTC

*SASSSVSYMY*WFQQKPGSSPRLLIY*DTSNLAS*GVPVRFSGSGS

GTSYSLTISRMEAEDAATFYC*QQWSSYPLT*FGAGTKLELK

Note: the shadow area is a light-chain variable region; the italic, bold and underlined areas are CDRs, which are VLCDR1, VLCDR2 and VLCDR3 in sequence.

A nucleotide sequence for coding the heavy chain of the monoclonal antibody C1;

(SEQ ID NO: 59)
ATGAAATGCAGCTGGGTCATCTTCTTCCTGATGGCAGTGGTTACAGGG

GTCAATTCAGAGGTTCAGCTGCAGCAGTCTGGGGCTGAGCTTGTGAGGC

CAGGGGCCTTAGTCAAGTTGTCCTGCAAAGCATCTGGCTTCAACATTAA

AGACTACTATATGCACTGGGTGAAGCAGAGGCCTGAAGAGGGCCTGGAG

TGGATTGGATGGATTGATCCTGAGAATGGTAATACTATATATGACCCGA

AGTTCCAGGGCAAGGCCAGTATAACAGCAGACACATCCTCCAACACAGT

CAGGCTGCAGCTCAGCAGCCTGACATCTGAGGACACTGCCGTCTATTAC

TGTGCTAGAGAGAGGGGCGCTTACTGGGGCCAAGGGACTCTGGTCACTG

TCTCTGCA

Note: the shadow area is a coding sequence of the heavy-chain variable region.

A nucleotide sequence for coding the light chain of the monoclonal antibody C1;

(SEQ ID NO: 60)
ATGGATTTTCAAGTGCAGATTTTCAGCTTCCTGCTAATCAGTGCCTCAG

TCATACTGTCCAGAGGACAAATTGTTCTCACCCAGTCTCCAGCAATCAT

GTCTGCATCTCCAGGGGAGAAGGTCACCATGACCTGCAGTGCCAGCTCA

AGTGTAAGTTACATGTACTGGTTCCAGCAGAAGCCAGGATCCTCCCCCA

GACTCCTGATTTATGACACATCCAACCTGGCTTCTGGAGTCCCTGTTCG

CTTCAGTGGCAGTGGGTCTGGGACCTCTTACTCTCTCACAATCAGCCGA

ATGGAGGCTGAAGATGCTGCCACTTTTTACTGCCAGCAGTGGAGTAGTT

ACCCGCTCACGTTCGGTGCTGGGACCAAGCTGGAGCTGAAA

Note: the shadow area is a coding sequence of the light-chain variable region.

The monoclonal antibodies N1, M1, M2, M3 and C1 obtained in the invention have specific CDRs, and are significantly different from existing reported monoclonal antibodies. The five monoclonal antibodies and a combination thereof can recognize all or most PVY isolates which have been reported, thus reducing the possibility of detection omissions; and the five monoclonal antibodies do not react with other congeneric viruses and non-congeneric viruses, thus reducing the possibility of detection errors. Therefore, the monoclonal antibodies and the combination thereof can realize accurate PVY detection.

The above embodiments are merely preferred ones of the application, and are not used to limit the invention. For those skilled in the art, various modifications and transformations of the application can be made. Any modifications, equivalent substitutions and improvements made based on the spirit and principle of the application should fall within the protection scope of the application.

What is claimed is:

1. A monoclonal antibody for detecting Potato virus Y (PVY), wherein the monoclonal antibody is monoclonal antibodies M1;
    the monoclonal antibody M1 has heavy-chain CDRs respectively as set forth in SEQ ID NO:7-9, and light-chain CDRs respectively as set forth in SEQ ID NO:10-12.

2. The monoclonal antibody according to claim 1, wherein a heavy-chain variable region of the monoclonal antibody M1 has an amino acid sequence as set forth in SEQ ID NO:33, and a light-chain variable region of the monoclonal antibody M1 has an amino acid sequence as set forth in SEQ ID NO:34.

3. The monoclonal antibody according to claim 1, wherein a heavy chain of the monoclonal antibody M1 has an amino acid sequence as set forth in SEQ ID NO:43, and a light chain of the monoclonal antibody M1 has an amino acid sequence as set forth in SEQ ID NO:44.

4. A combination of monoclonal antibodies for detecting PVY, wherein the combinations of monoclonal antibodies comprises: monoclonal antibody M1 according to any one of claims 1-3, and monoclonal antibody M2, wherein the monoclonal antibody M2 comprises the heavy-chain CDRs as set forth in SEQ ID NO:13-15, respectively, and light-chain CDRs as set forth in SEQ ID NO:16-18, respectively.

5. The combinations of monoclonal antibodies according to claim 4, wherein a heavy-chain variable region of the monoclonal antibody M2 has an amino acid sequence as set forth in SEQ ID NO:35, and a light-chain variable region of the monoclonal antibody M2 has an amino acid sequence as set forth in SEQ ID NO:36.

6. An ELISA kit for detecting PVY, wherein the ELISA kit comprises the combinations of monoclonal antibodies according to claim 4.

* * * * *